United States Patent
Asikainen et al.

(10) Patent No.: US 10,301,276 B2
(45) Date of Patent: May 28, 2019

(54) METHOD OF PRODUCING FURAN CARBOXYLATES FROM ALDARIC ACIDS BY USING SOLID HETEROGENEOUS CATALYST

(71) Applicant: Teknologian tutkimuskeskus VTT Oy, Espoo (FI)

(72) Inventors: Martta Asikainen, Espoo (FI); David Thomas, Espoo (FI); Ali Harlin, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 15/566,759

(22) PCT Filed: Apr. 18, 2016

(86) PCT No.: PCT/FI2016/050254
§ 371 (c)(1),
(2) Date: Oct. 16, 2017

(87) PCT Pub. No.: WO2016/166421
PCT Pub. Date: Oct. 20, 2016

(65) Prior Publication Data
US 2018/0086728 A1    Mar. 29, 2018

(30) Foreign Application Priority Data
Apr. 17, 2015  (FI) ..................... 20155285

(51) Int. Cl.
*B01J 21/04* (2006.01)
*C07D 307/68* (2006.01)
*C08G 63/16* (2006.01)
*B01J 21/06* (2006.01)
*B01J 21/08* (2006.01)
*B01J 29/03* (2006.01)
*B01J 31/02* (2006.01)
*B01J 31/06* (2006.01)
*C08G 63/672* (2006.01)
*B01J 37/02* (2006.01)

(52) U.S. Cl.
CPC ............ *C07D 307/68* (2013.01); *B01J 21/04* (2013.01); *B01J 21/066* (2013.01); *B01J 21/08* (2013.01); *B01J 29/0308* (2013.01); *B01J 31/0225* (2013.01); *B01J 31/06* (2013.01); *B01J 37/0203* (2013.01); *C08G 63/16* (2013.01); *C08G 63/672* (2013.01); *B01J 2229/32* (2013.01)

(58) Field of Classification Search
USPC ......................................................... 528/306
See application file for complete search history.

(56) References Cited

U.S. PATENT DOCUMENTS

2014/0024793 A1   1/2014  Matsuo et al.
2014/0295508 A1  10/2014  Yoshikuni et al.

FOREIGN PATENT DOCUMENTS

| FR | 2723945 A1 | 3/1996 |
| FR | 2723946 B1 | 3/1996 |
| JP | 2008127282 A | 6/2008 |
| WO | WO2011063500 A1 | 6/2011 |

OTHER PUBLICATIONS

Lewkoswski J.: "Convenient synthesis of furan-2,5-dicarboxylic acid and its derivates", Polis Journal of Chemistry, 2001, vol. 75, No. 12, pp. 1943-1946.

Ribeiro M. et al.: "Cooperative effect of cobal acetylacetonate and silica in the catalytic cyclization and oxidation of fructose to 2,5-furandicarboxylic acid", Catalysis Communications 4, 2003, pp. 83-86.

Werpy T. et al.: "Top Value Added Chemicals from Biomass", U.S. Department of Energy-Energy Efficiency and Renewable Energy, 2004, vol. 1, pp. 26-28.

Yoichi T. et al: "One-step synthesis of dibutyl furandicarboxylates from galactaric acid", Chemistry Letters, Jan. 5, 2008, vol. 37, No. 1, pp. 50-51.

*Primary Examiner* — Terressa Boykin
(74) *Attorney, Agent, or Firm* — Seppo Laine Oy

(57) ABSTRACT

According to an example aspect of the present invention, there is provided a method of producing furan carboxylates from aldaric acids in the presence of a solid heterogeneous catalyst and a solvent with short reaction time. The feedstock for the production is a stable compound, which allows industrial scaling of the process. Solid acid catalyst and sustainable solvent provide considerable reduction of toxic waste compared to traditional methods, and recyclability.

12 Claims, No Drawings

METHOD OF PRODUCING FURAN CARBOXYLATES FROM ALDARIC ACIDS BY USING SOLID HETEROGENEOUS CATALYST

FIELD

The present invention relates to a synthetic method of producing furan carboxylates by using catalysts. More precisely, the present technology describes an environmentally friendly production method of furan carboxylates and furan dicarboxylates from aldaric acids with solid catalysts, which do not generate toxic waste.

BACKGROUND

Carbohydrates are excellent starting materials for the production of bulk and specialty chemicals. Intelligent usage of the intrinsic functionality is already present in carbohydrates. Furan chemicals (for example, 2-hydroxymethyl furan (HMF)) are known to have high potential as a starting material for industry.

Furan carboxylates, such as 2,5-furandicarboxylic acid (FDCA), have been traditionally used e.g. in pharmacology, where its diethyl ester has showed a strong anesthetic activity. FDCA is also a very powerful chelating agent. In medicine, it is e.g. used to treat kidney stones, but also in the preparation of grafts having biological properties similar to those of natural tissues, and which are characterized by a lack of rejection after transplantation.

FDCA has also been used as a basic monomer in the manufacture of polymers such as polyesters, polyamides, co-polymers or polyurethanes, e.g. for improving their mechanical properties. In polyesters, it is likely to be used in replacement of phthalates. In view of such a possibility, the FDCA has been ranked among the 12 raw materials with the greatest industrial potential (Werpy and Peterson, 2004).

Furan carboxylates are also realistic alternative to terephthalic acid, which is a monomer used in polyethylene terephthalate production and used for example in plastic bottles. The bio-based furan carboxylate solution should therefore be both chemically efficient and environmentally sustainable.

Monocarboxylates such as 2-furoic acid finds uses as a monomer, preservative, flavouring agent, and it may have use in optic technologies. The 2-furoic acid esters can be used for example as bio-based fuel components.

Traditionally furan carboxylates are prepared using either unstable intermediates (HMF) or from aldaric acids by using excess strong mineral acids. Both of these routes limit the scalability of the process and produce highly toxic waste, which is damaging to the environment.

There are currently two main routes to furan carboxylates. First route is through synthesis of HMF and transformation to furan carboxylate. This process is limited on scale because of the instability of the intermediate. Many methods exist but are hampered by this limiting factor. Second route is through aldaric acids via use of strong mineral acids. There are two main problems with this route, firstly the yields are limited to around 60% and secondly the acidic reaction solvent cannot be recycled and is highly toxic to the environment.

French patent FR 2723945 (1996) describes furan synthesis from galactaric acid with and excess of strong mineral acids (HBr, HCl, $H_2SO_4$, $H_2NO_4$, $H_2PO_4$). Yields vary between 35 to 66%, but the reaction time is long (9 to 10 hours) and the method produces toxic waste.

Furan carboxylates have promising industrial potential. However, their traditional synthesis methods have several drawbacks, such as operating under relative severe conditions, generating large amounts of toxic waste and resulting poor yields. Thus, there is a need for a sustainable, quick and easily up-scalable production process for furan (mono- and di-) carboxylates.

SUMMARY OF THE INVENTION

The invention is defined by the features of the independent claims. Some specific embodiments are defined in the dependent claims.

According to a first aspect of the present invention, there is provided a sustainable method for producing furan carboxylates from aldaric acids.

According to a second aspect of the present invention, there is provided an easily up-scalable process for producing building blocks and platform chemicals from aldaric acids for use e.g. in the green production of polyethylene furanoate, a bio-based replacement for polyethylene terephthalate.

These and other aspects, together with the advantages thereof over known solutions are achieved by the present invention, as hereinafter described and claimed.

The method according to an embodiment of the present invention is mainly characterized by what is stated in the characterizing part of claim 1.

One advantage of the present invention is that the method can be directed to produce either furan monocarboxylate or furan dicarboxylate. By using solid acid catalysts the production of considerable amounts of toxic waste is greatly reduced compared to the traditional methods in the art. An additional advantage is that the reaction times of the process are short.

Next, the present technology will be described more closely with reference to certain embodiments.

EMBODIMENTS

In the present context, the term "heterogeneous catalyst" comprises catalysts having a different phase from that of the reactants. "Phase" herein refers not only to solid, liquid and gas but also to e.g. immiscible liquids.

The present technology describes a method of producing furan carboxylates and furan dicarboxylates from wide raw material base, such as from sugars, uronic acids and aldaric acids from various C6-sugars.

According to an embodiment, the method of producing esters of furan carboxylates and furan dicarboxylates from aldaric acids comprises mixing together an aldaric acid, a solid heterogeneous catalyst and a solvent in a temperature of 130 to 250° C., such as 200 to 230° C., to form a solution comprising furan esters.

According to another embodiment, the method also comprises recovering a desired furan ester(s) and/or acid(s) from the solution. Furan esters can be used directly as feedstock for polymerisation to, for example, polyethylene furanoate.

Aldaric acids are a group of sugar acids, where the terminal hydroxyl and aldehyde groups of the sugars have been replaced by terminal carboxylic acids, and are characterized by the formula HOOC—$(CHOH)_n$—COOH, n being an integer from 1 to 10, in particular 1 to 4, such as 3 or 4. The nomenclature of the aldaric acids is based on the sugars from which they are derived. For example, glucose is oxidized to glucaric acid, galactose to galactaric acid and xylose to xylaric acid. Unlike their parent sugars, aldaric acids have the same functional group at both ends of their carbon chain.

One important aspect of the present invention is the use of a heterogeneous catalyst, which has been found to produce little waste, is easy to separate from the reaction mixture and is also recyclable. Heterogeneous catalysts also permit continuous processing and enable short reaction times in the method herein described.

According to another embodiment, the present method includes the steps of:
- charging an aldaric acid, a non-toxic heterogeneous solid acid catalyst and an organic solvent into a pressure reaction vessel to form a reaction mixture,
- heating the reaction mixture to a temperature of 130 to 250° C. in said reaction vessel,
- maintaining the temperature in the reaction vessel for a pre-determined reaction time,
- cooling the reaction down to room temperature between 20 and 25° C.,
- collecting the reaction mixture,
- recovering the desired furan ester(s) and/or acid(s) from the reaction mixture.

According to a further embodiment, furan esters are converted into corresponding acids after being recovered from the reaction.

The method as herein described produces stable and crystalline intermediates, compared for example to the traditional HMF-route.

According to a further embodiment, it is preferred to use a solvent vapor pressure of 5 to 50 bars, preferably 15 to 30 bars in the reaction vessel. The reactions can be carried out either under air or inert gases.

According to an even further embodiment, the reaction time in the present production process is short, more precisely as low as 0.25 to 9 hours, preferably 0.25 to 4 hours, more preferably 0.5 to 2 hours, and most suitably about 1 hour.

One suitable raw material or feedstock for furan carboxylate production according to one embodiment is galactaric acid having formula I:

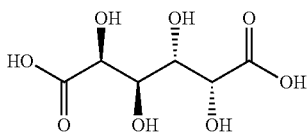 [SMILES: O=C(O)[C@@H](O)[C@H](O)[C@H](O)[C@@H](O)C(=O)O]

I

The method as herein described produces esters of 2-Furoic acid and 2,5-Furandicarboxylic acid (FDCA) from the starting material, when alcohols are used as solvents. The esters may be converted into corresponding acids by methods known in the art. In the case of other solvents, such as water, acids are produced directly. Such acids have formulas II and III, respectively:

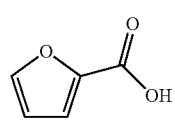

II

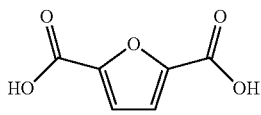 [SMILES: O=C(O)c1ccc(C(=O)O)o1]

III

Another suitable raw material or feedstock for furan carboxylate production according to another embodiment is glucaric acid ester having formula XII:

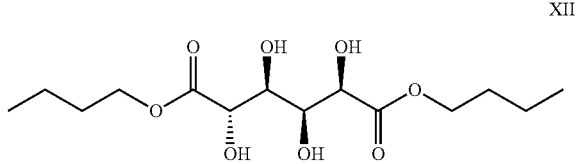

XII

Thus, according to one embodiment of the present invention, the aldaric acid used as raw material or feedstock is either galactaric acid or glucaric acid in either free acid or ester form.

According to one embodiment, the catalyst is selected from solid sulfonic acids on different polymer, silica, alumina or zirconia carriers. More precisely, the catalyst is selected from perfuorosulfonic acid polymers (such as Nafion NR50), phenyl sulfonic acid ethyl sulfide silica, sulfonated alumina catalyst and sulfonated zirconia catalyst.

According to another embodiment, the solvent is an alcohol solvent, selected from monovalent or polyvalent $C_1$-$C_6$ alcohols, or any combination thereof. Examples of suitable alcohols are ethanol, 1-butanol or 1-pentanol, or any combination thereof. However, also water and tetrahydrofuran (THF) may be used as solvent.

The purification (i.e. recovering) of the produced products comprises filtering any solid precipitate, washing the precipitate with alcohol and drying the washed product(s) for example by evaporation. The organic phase having the desired product(s) of the present invention is subsequently evaporated and then purified, for example, by silica column chromatography. The results are confirmed by further analysis methods generally known in the art.

According to one embodiment, the present method produces less waste than traditional methods. Reference is made for example to FR 2723945, where 70 g of galactaric acid in 1 liter of HBr acid is used. With HBr density of 1.49 this means that 1.49 kg of HBr is consumed when converting 70 g of galactaric acid to Furan dicarboxylic acid. The present method does not require strong mineral acids and neither produces such waste.

According to a further embodiment, the catalyst and the solvent are regenerated after the reaction from a reaction mixture and thus reusable. The solvent can be, for example, distilled and reused after the reaction. The catalyst can be regenerated after separating it from the reaction mixture by first washing and then drying the catalyst.

The furan product obtained by the method of the present invention can also be used directly, for example as a fuel additive, without removing the catalyst from the reaction mixture as the amount of the catalyst is low. Direct use is even more appealing after the catalyst has been removed, for example by filtration.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in generating a full value chain from the forest industry, agriculture, or food industry side streams to platform chemicals and end applications. In principle, this chain comprises production of aldaric acids from aldoses and side-stream carbohydrates, converting the aldaric acids to dicarboxylic acids, which in turn are used as platform chemicals for various bio-based applications, such as bio-based polyesters and nylon. According to one example, the present method produces 2,5-Furandicarboxylic acid for use in the production of polyethylene furanoate.

EXAMPLES

TABLE 1

Reactants and reaction products (I) Galactaric acid (II) 2,5-Furandicarboxylic acid (III) 2-Furoic acid (IV) 2,5-Furandicarboxylic acid di-n-butyl ester (V) 2,4-Furandicarboxylic acid di n-butyl ester (VI) 2,3-Furandicarboxylic acid di-n-butyl ester TABLE 1-continued Reactants and reaction products (VII) 2-Furoic acid n-butyl ester (VIII) 2,5-Furandicarboxylic acid di-ethyl ester (IV) 2-Furoic acid ethyl ester (X) 2,5-Furandicarboxylic acid di-n-pentyl ester (XI) 2-Furoic acid n-pentyl ester (XII) Glucaric acid di-n-butyl ester

General Method for the Production of Furan Carboxylates from Aldaric Acids

To a pressure reactor equipped with magnetic stirring bar and Teflon liner were charged the solvent (20 ml), galactaric acid (2.0 g) and solid catalyst (1.0 g). The reactor was closed and heated in an oil bath to the reaction temperature for indicated time. The reaction could be performed under air or inert gases. After the indicated reaction time, the solid and liquid phases were separated, and organic compounds from the solid phase were extracted with hot solvent. The fractions were analysed with GC-FID for quantitative analysis of each furan compound.

The GC-FID analyses were done with Shimadzu GC-1020 Plus Gas Chromatograph. The column used was ZB-5HT Inferno and the temperature program 100° C./1 min→10° C./min to 280° C./hold time 1 min→30° C./min to 350° C./hold time 5 min. Injector temperature 320° C., detector temperature 380° C., carrier gas helium, pressure 100.2 kPa, total flow 103.8 ml/min, column flow 1.00 ml/min, linear velocity 27.5 cm/sec, purge flow 3.0 ml/min, injection volume 1.0 µl, split ratio 100. All reaction fractions were silylated with standard methods prior to GC-FID analysis.

Example 1

The general method was used, with a commercial catalyst phenyl sulfonic acid ethyl sulfide silica and 1-butanol as solvent. The reaction time was 30 min and reaction temperature was 230° C. After the reaction the solid fraction was removed by filtration, and the liquid fraction was concentrated in a rotary evaporator. The evaporated residue was purified with flash column chromatography (30% ethyl acetate in hexane) with silica gel 60. Following products were obtained: Compound IV (0.43 g) and a mixture of compounds V and VI (0.10 g).

Compound IV was analysed with NMR and FT-IR to give following: $^1$H NMR (500 MHz, DMSO-d$_6$): δ=7.41 (s, 2H, CH×2), 4.29 (t, 4H, J=6.56 Hz, CH$_2$×2), 1.70-1.64 (m, 4H, CH$_2$×2), 1.42-1.35 (m, 4H, CH$_2$×2), 0.92 (t, 6H, J=8.42 Hz, CH$_3$×2); $^{13}$C NMR (125.8 MHz, DMSO-d$_6$): δ=157.5, 146.2, 119.0, 65.0, 30.1, 18.6, 13.6; IR (cm$^{-1}$) ν: 3118 (small), 2958 (medium), 2933, 2871, 1723 (large C=O), 1575, 1267, 1150, 817.

Example 2: Catalyst Phenyl Sulfonic Acid Ethyl Sulphide Silica

The general method was repeated using a commercial catalyst, phenyl sulfonic acid ethyl sulfide silica, and 1-butanol as solvent. The conditions and the obtained reaction products are given in Table 2.

TABLE 2

| Entry | Reaction conditions T (° C.) | t (h) | Yield II | Yield IV | Yield III | Yield VII |
|---|---|---|---|---|---|---|
| 2.1 | 200 | 4 |  | 5.2 |  | 4.3 |
| 2.2 | 230 | 0.5 | 1.8 | 23.8 | 0.9 | 5.9 |
| 2.3 | 230 | 1 | 0.3 | 24.6 | 2 | 11.5 |
| 2.4 | 230 | 4 | 3.4 | 25.2 | 3.9 | 24.5 |

The general method was repeated with commercial catalyst phenyl sulfonic acid ethyl sulfide silica and 1-butanol as solvent. Reaction conditions were 230° C. and 1 hour reaction time, varying the catalyst quantity. The conditions and the obtained reaction products are given in Table 3.

TABLE 3

| Entry | Catalyst quantity (g) | Yield II (HO-furan-COOH / HOOC-furan-OH) | Yield IV (butyl furan dicarboxylate) | Yield III (furan-2-COOH) | Yield VII (butyl furan-2-carboxylate) |
|---|---|---|---|---|---|
| 3.1 | 0.5 | 0.7 | 12.4 | 0.5 | 2.4 |
| 3.2 | 1 | 0.3 | 24.6 | 2 | 11.5 |
| 3.3 | 2 | 3.1 | 19.4 | 1.5 | 7.9 |

Example 3: Catalyst Sulfonic Acid Functionalised Silica MCM-41

Preparation of sulfonic acid functionalised silica catalyst: Calcinated MCM-41 silica (2.0 g) was mixed with toluene (60 ml) and mercaptyl trimethoxysilane (2.0 ml) and the reaction was refluxed for 24 hours. Solids were filtered, washed with methanol, and dried in a vacuum oven. The resulting functionalised silica was mixed with 30% hydrogen peroxide (40 ml) for 24 hours at room temperature. Solids were filtered and washed with methanol and dried in a vacuum oven.

The general method was repeated with sulfonic acid functionalised silica catalyst (prepared as described above) and 1-butanol as solvent. The conditions and the obtained reaction products are given in Table 4.

TABLE 4

| Entry | Reaction conditions T (° C.) | t (h) | Yield II | Yield IV | Yield III | Yield VII |
|---|---|---|---|---|---|---|
| 4.1 | 200 | 4 |  | 3.3 |  | 0.4 |
| 4.2 | 230 | 2 | 1.1 | 12.0 | 3.1 | 18.6 |

Example 4: Catalyst Perfluorosulfonic Acid Polymer, Such as Nafion NR50

The general method was repeated with commercial catalyst Nafion NR50 and 1-butanol as solvent. Reaction conditions were 230° C. and 2 hours reaction time, varying the concentration of galactaric acid. The conditions and the obtained reaction products are given in Table 5.

TABLE 5

| Entry | Galactaric acid concentration (g/ml) | Yield II | Yield IV | Yield III | Yield VII |
|---|---|---|---|---|---|
| 5.1 | 0.05 | 1.5 | 7.6 | 1.6 | 1.8 |
| 5.2 | 0.1 | 1.6 | 5.8 | 3.1 | 12.2 |
| 5.3 | 0.2 | 2.3 | 3.8 | 0.6 | 10.8 |

Example 5: Catalyst Sulfonated Zirconia

Preparation of sulfonated zirconia catalyst: Zirconium IV hydroxide (2.0 g) and sulfuric acid (1N, 30 ml) were stirred at room temperature for 3 hours and vacuum filtered. The catalyst was dried at 40° C. at 160 mbar. The solids were ground to give a white powder in 30% yield. The product was calcinated at 600° C. for 2 hours.

The general method was repeated with sulfonated zirconia catalyst (prepared as described above) and 1-butanol as solvent. The conditions and the obtained reaction products are given in Table 6.

TABLE 6

| Entry | Reaction conditions T (° C.) | Reaction conditions t (h) | Yield II 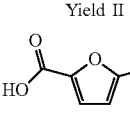 | Yield IV 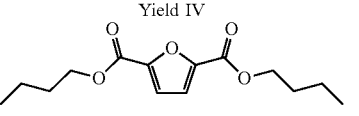 | Yield III 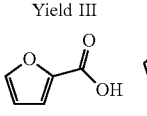 | Yield VII 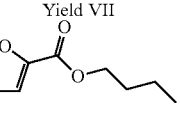 |
|---|---|---|---|---|---|---|
| 6.1 | 230 | 2 | 0.1 | 5.1 | 0.6 | 4.3 |

Example 6: Catalyst Sulfonated Alumina

Preparation of sulfonated alumina catalyst 1: γ-alumina (3.0 g) is mixed with p-toluenesulfonic acid (1.3 g) in water (2.2 g) and heating to 140 C for 4 hours. The slurry was filtered and washed with water to give a pale purple powder product in 58% mass recovery after vacuum drying at 40° C.

Preparation of sulfonated alumina catalyst 2: Alumina (Catapol A, 5.0 g) mixed with sulfuric acid (50 ml, 1.6M) for 1 hour. Purified by soxhlet extraction with water over 20 hours to give product in 31% mass recovery after vacuum drying at 40° C.

The general method was repeated with sulfonated alumina catalysts 1 and 2 (prepared as described above) and 1-butanol as solvent. Reaction conditions were 230° C. and 2 hours reaction time. The obtained reaction products are given in Table 7.

TABLE 7

| Entry | Catalyst | Yield II 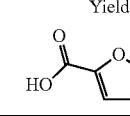 | Yield IV 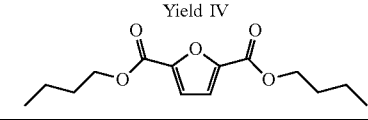 | Yield III 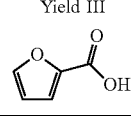 | Yield VII 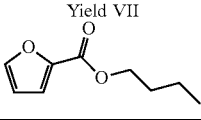 |
|---|---|---|---|---|---|
| 7.1 | Sulfonated alumina catalyst 1 | | 3.0 | 0.8 | 12.6 |
| 7.2 | Sulfonated alumina catalyst 2 | | 2.3 | 2.8 | 10.4 |

Example 7: Catalyst Phenyl Sulfonic Acid Ethyl Sulfide Silica with Solvents Water, Tetrahydrofuran, Ethanol and 1-Pentanol The general method was repeated with commercial catalyst phenyl sulfonic acid ethyl sulfide silica and different solvents. Reaction conditions were 230° C. and 1 hour reaction time. The obtained reaction products are given in Table 8.

TABLE 8

| Entry | Solvent | Yield II 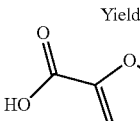 | Yield III 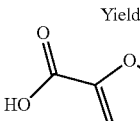 |
|---|---|---|---|
| 8.1 | Water | 1.1 | 2.4 |
| 8.2 | Tetrahydrofuran (THF) | 7.6 | 8.4 |

The general method was repeated with commercial catalyst phenyl sulfonic acid ethyl sulfide silica and ethanol as solvent. Reaction conditions were 210° C. and 1 hour reaction time. The obtained reaction products are given in Table 9.

TABLE 9

| Entry | Solvent | Yield II 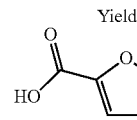 | Yield VIII 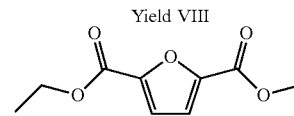 | Yield III 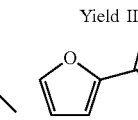 | Yield IV 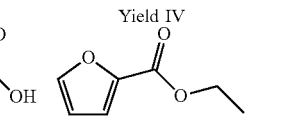 |
|---|---|---|---|---|---|
| 9.1 | Ethanol | 1.9 | 1.1 | 4.5 | 3.1 |

The general method was repeated with commercial catalyst phenyl sulfonic acid ethyl sulfide silica and 1-pentanol as solvent. Reaction conditions were 230° C. and 1 hour reaction time. The obtained reaction products are given in Table 10.

TABLE 10

| Entry | Solvent | Yield II 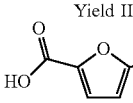 | Yield X 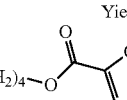 | Yield III 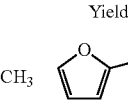 | Yield XI 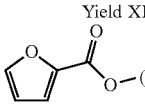 |
|---|---|---|---|---|---|
| 10.1 | 1-Pentanol | 0.7 | 13.9 | 0.6 | 16.7 |

Example 8: Catalyst Phenyl Sulfonic Acid Ethyl Sulfide Silica with Glucaric Acid Glucaric acid potassium salt (5.0 g), Amberlyst 15 (10 g) and n-Butanol (100 ml) were charged in the reaction flask and heated to 75° C. for 22 hours with magnetic stirring. The mixture was filtrated while hot and the filtrate was concentrated in a rotary evaporator to yield Compound XII, glucaric acid di-n-butyl ester (3.3 g).

The general method was repeated with glucaric acid di-n-butyl ester as feedstock, using commercial catalyst phenyl sulfonic acid ethyl sulfide silica and 1-butanol as solvent. The reaction conditions and obtained reaction products are given in Table 11.

TABLE 11

| Entry | Feedstock | Reaction conditions T (° C.) | t (h) | Yield IV 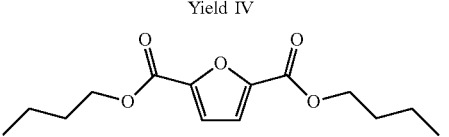 | Yield VII 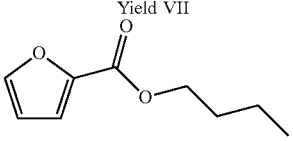 |
|---|---|---|---|---|---|
| 11.1 | Compound XII | 230 | 1 | 28.8 | 16.1 |

Example 9: Methanol Solvent

The general method was used with galactaric acid (I) used as the aldaric acid. The reaction time was 1 hour and the yields are shown in Table 12.

TABLE 12

| Entry | Solvent | Yield II 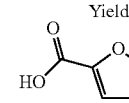 | Yield X 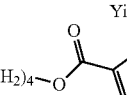 | Yield III 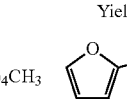 | Yield XI 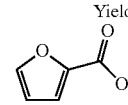 |
|---|---|---|---|---|---|
| 12.1 | methanol | 4.0 | 0.5 | 0.3 | 0.0 |

Example 10: Extended Time

The general method was used, but the reaction time was extended to 9 hours. Galactaric acid (I) was used as the aldaric acid in butanol solvent. Yields are shown in Table 13.

TABLE 13

| Entry | Solvent | Reaction time (h) | Yield II 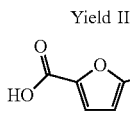 | Yield X 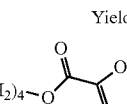 | Yield III 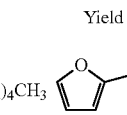 | Yield XI 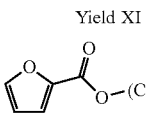 |
|---|---|---|---|---|---|---|
| 13.1 | 1-butanol | 9 | 0.4 | 4.1 | 0 | 0 |

Example 11: Catalyst Charge Reduced from the 1-2 Equivalents Down to 0.1 Equivalents The general method was used, but catalyst charge was dropped to 0.1 equivalents. Galactaric acid (I) was used as the aldaric acid in butanol solvent with reaction time of 1 hour. The yields are shown in Table 14.

TABLE 14

| Entry | Solvent | Catalyst (m %) | Yield II 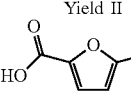 | Yield X 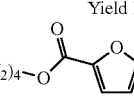 | Yield III 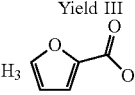 | Yield XI 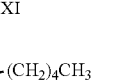 |
|---|---|---|---|---|---|---|
| 14.1 | 1-butanol | 10 | 0 | 7.85 | 0 | 2.8 |

Example 12: Temperature Reduced to 130° C.

The general method was used with galactaric acid (I) as the aldaric acid in butanol solvent with the temperature of 130° C. and reaction time of 1 hour. Yields are shown in Table 15.

TABLE 15

| Entry | Solvent | Reaction temperature (° C.) | Yield II 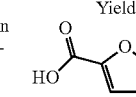 | Yield X 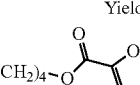 | Yield III 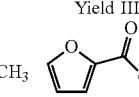 | Yield XI 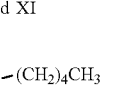 |
|---|---|---|---|---|---|---|
| 15.1 | 1-butanol | 130 | 3.1 | 5.2 | 0 | 0 |

Example 13: Glucaric Acid Di-n-Butyl Ester and Methanol Solvent

The general method was used using glucaric acid di-n-butyl ester (XII) and methanol as the solvent. The reaction time was 1 hour and the yields are shown in Table 16.

TABLE 16

| Entry | Solvent | Yield II 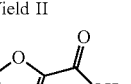 | Yield X 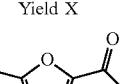 | Yield III 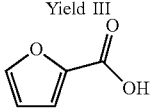 | Yield XI  |
|---|---|---|---|---|---|
| 16.1 | methanol | 0.5 | 9.8 | 1.1 | 0 |

Example 14: Glucaric Acid Di-n-Butyl Ester and Ethanol

The general method was used using glucaric acid di-n-butyl ester (XII) and ethanol as the solvent. The reaction time was 1 hour and the yields are shown in Table 17.

TABLE 17

| Entry | Solvent | Yield II 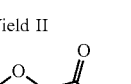 | Yield X 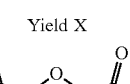 | Yield III 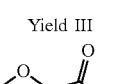 | Yield XI  |
|---|---|---|---|---|---|
| 17.1 | ethanol | 1.3 | 20.7 | 0.5 | 6.4 |

Example 15: Glucaric Acid Di-n-Butyl Ester and Lowering the Catalyst Charge

The general method was used, but with 0.1 equivalents of charge. Glucaric acid di-n-butyl ester (XII) as the aldaric acid and a reaction time of 1 hour was used. The yields are shown in Table 18.

TABLE 18

| Entry | Solvent | Catalyst (m %) | Yield II  | Yield X  | Yield III | Yield XI  |
|---|---|---|---|---|---|---|
| 18.1 | butanol | 10 | 0.1 | 4.6 | 5.8 | 0 |

CITATION LIST

Patent Literature

FR 2723945

Non Patent Literature

Werpy, T., Peterson, G., 2004. Top Value Added Chemicals from Biomass, Vol. 1 pp. 26-28.

The invention claimed is:

1. A method of producing furan carboxylates and furan dicarboxylates from aldaric acids, comprising mixing together an aldaric acid, a solid heterogeneous catalyst selected from the group consisting of perfluorosulfonic acid polymer, phenyl sulfonic acid ethyl sulfide silica, sulfonated alumina catalyst and sulfonated zirconia catalyst, and a solvent at temperature between 130 and 250° C., and by applying a reaction time of 0.25 to 9 hours, to form a solution comprising furan esters.

2. The method of claim 1, further comprising the steps of:
charging an aldaric acid, a non-toxic heterogeneous solid acid catalyst and an organic solvent into a pressure reaction vessel to form a reaction mixture,
heating the reaction mixture to temperature between 130 and 250° C. in said reaction vessel,
maintaining the temperature in the reaction vessel for a pre-determined reaction time, and
recovering the desired furan ester(s) and/or acid(s) from the reaction mixture.

3. The method of claim 1, further comprising applying a reaction time of 0.25 to 4 hours.

4. The method of claim 1, wherein the aldaric acid is either galactaric acid or glucaric acid in either free acid or ester form.

5. The method of claim 1, wherein the solvent is water or tetrahydrofuran (THF) or mixtures thereof.

6. The method of claim 1, wherein the solvent is an alcohol solvent selected from monovalent or polyvalent $C_1$-$C_6$ alcohols, or any combination thereof.

7. The method of claim 1, wherein the solvent is selected from ethanol, 1-butanol or 1-pentanol, or any combination thereof.

8. The method of claim 1, further comprising producing an ester of 2,5-Furandicarboxylic acid (FDCA).

9. The method of claim 1, wherein a solvent vapor pressure is between 5 and 50 bars.

10. The method of claim 1, further comprising recovering the catalyst and/or the solvent from the reaction solution.

11. The method of claim 1, further comprising applying a reaction time of 0.5 to 2 hours.

12. The method of claim 1, further comprising applying a reaction time of about 1 hour.

* * * * *